US009855463B2

(12) United States Patent
Erkkila et al.

(10) Patent No.: US 9,855,463 B2
(45) Date of Patent: Jan. 2, 2018

(54) MANAGING PHYSIOLOGICAL EXERCISE DATA

(71) Applicant: Polar Electro Oy, Kempele (FI)

(72) Inventors: Mika Erkkila, Oulu (FI); Riikka Rae, Oulu (FI); Tomi Thurlin, Oulu (FI); Tuomo Korva, Oulu (FI); Tony Manninen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 361 days.

(21) Appl. No.: 14/157,163

(22) Filed: Jan. 16, 2014

(65) Prior Publication Data

US 2015/0196801 A1 Jul. 16, 2015

(51) Int. Cl.
A63B 24/00 (2006.01)
A63B 71/06 (2006.01)
G06F 19/00 (2011.01)

(52) U.S. Cl.
CPC ...... *A63B 24/0062* (2013.01); *A63B 71/0619* (2013.01); *G06F 19/322* (2013.01); *G06F 19/3481* (2013.01); *A63B 2024/0065* (2013.01)

(58) Field of Classification Search
None
See application file for complete search history.

(56) References Cited

U.S. PATENT DOCUMENTS

| 2005/0070809 A1 | 3/2005 | Acres |
| 2006/0200009 A1 | 9/2006 | Wekell et al. |
| 2008/0096726 A1* | 4/2008 | Riley ............... A63B 24/0006 482/8 |
| 2009/0262088 A1* | 10/2009 | Moll-Carrillo .... A63B 24/0062 345/173 |
| 2011/0152695 A1 | 6/2011 | Granqvist et al. |
| 2012/0254934 A1* | 10/2012 | McBrearty ......... G06F 19/3481 725/118 |
| 2014/0337451 A1* | 11/2014 | Choudhary ............ H04L 51/00 709/206 |

FOREIGN PATENT DOCUMENTS

| EP | 2610808 A1 | 7/2013 |
| GB | 2495014 A | 3/2013 |

OTHER PUBLICATIONS

European Search Report for corresponding European Application No. EP15150765, pp. 1-3 (dated Mar. 25, 2015).
Summons to attend oral proceedings issued in corresponding European Application No. 15150765.4, dated May 18, 2017.

* cited by examiner

*Primary Examiner* — Milap Shah
*Assistant Examiner* — Robert T Clarke, Jr.
(74) *Attorney, Agent, or Firm* — Hoffmann & Baron, LLP

(57) ABSTRACT

A method includes acquiring physiological exercise data from a plurality of physiological exercise sensors applied by a group of exercisers; determining a performance metric for each exerciser on the basis of the acquired physiological exercise data; detecting whether or not a predetermined common target is met on the basis of the performance metrics; and triggering an event upon detecting that the predetermined common target is met.

14 Claims, 5 Drawing Sheets

MANAGING PHYSIOLOGICAL EXERCISE DATA

BACKGROUND

Field

The invention relates generally to managing exercise data from a plurality of exercisers.

Description of the Related Art

There may be situations where several exercisers are exercising simultaneously. One example may be a gym environment, where an instructor may lead a group of exercisers. In such group activity it may be important to motivate the exercisers to perform well.

SUMMARY

According to an aspect of the invention, there is provided a computing device as specified in claim 1.

According to an aspect of the invention, there is provided a method as specified in claim 13.

According to an aspect of the invention, there is provided a computer program product as specified in claim 14.

According to an aspect of the invention, there is provided a computer-readable distribution medium carrying the above-mentioned computer program product.

According to an aspect of the invention, there is provided an apparatus comprising means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
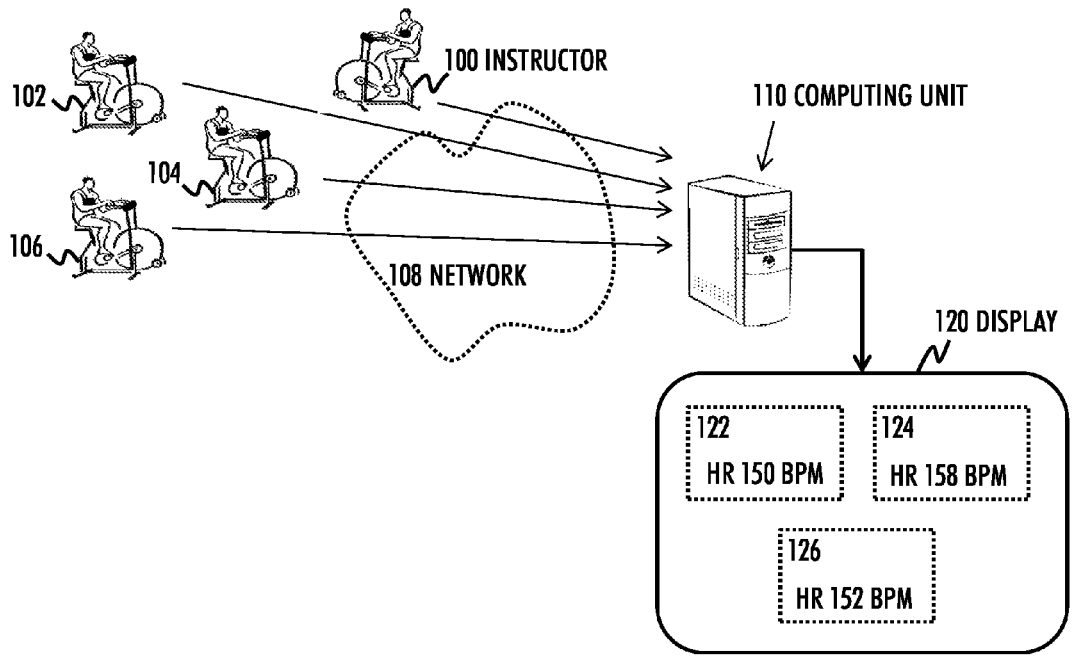
FIG. 1 presents an example group exercise scenario.

As shown in FIG. 1, in a group training session, such as in a gym session, a group of persons 102-108 exercise simultaneously under the control of an instructor 100. The instructor 100 may give group instructions to the group according to a predetermined or ad hoc training plan. The exercisers 102-108 may be wearing physiological exercise sensors, such as heart activity sensors. In an embodiment, the heart activity sensor comprises at least one electrical or optical sensor to measure heart activity of the exerciser. Other types of exercise sensors may also be applied by the exercisers 102-108. These may include, e.g., a cadence sensor and a power sensor, to mention only a few. Further, the exercisers 102-108 may have personal training computers, which the exercisers 102-106 may wear on their wrists or attach to the exercise device. From the training computers, the exercisers 102-108 may monitor training parameters that characterize their physiological state. This may be detected from one or more performance metrics, such as heart rate information, e.g. by monitoring how the heart rate changes as the training session goes on.

However, monitoring a relatively small personal training computer may not be easy during the active training session. Therefore, it may also be that the group members 102-108 may monitor their personal performance metrics from a common screen/display 120 viewable to all the exercisers 102-108 while performing the group exercise. The display screen 120 may include a section 122-128 for each individual exerciser 102-108. The individual section 122 may correspond to the exerciser 102, the section 124 to the exerciser 124, etc. The individual sections 122-128 may show the performance metric of the corresponding exerciser 102-108 on the basis of the measured exercise sensor data from the exercise sensors.

The exercise data of each individual exerciser 102-108 may be transmitted via a wireless network 110 to a computing unit 110, where the exercise data may be processed to obtain the performance metrics, for example. The computing device 110 may further show the exercise data on the correct sections 122-128 of the common screen 120, which may be coupled to the computing unit 110. In this way, as shown in FIG. 1, each exerciser 102-108 may see how the other exercisers 102-108 in the group are respond to the current pace of the exercise or how hard the other exercisers 102-108 are exercising, for example. This may motivate the exercisers 102-108 to perform better during the exercise so as to get the most out of the training session. However, better and more motivating features may still be of use.

Figure 2:
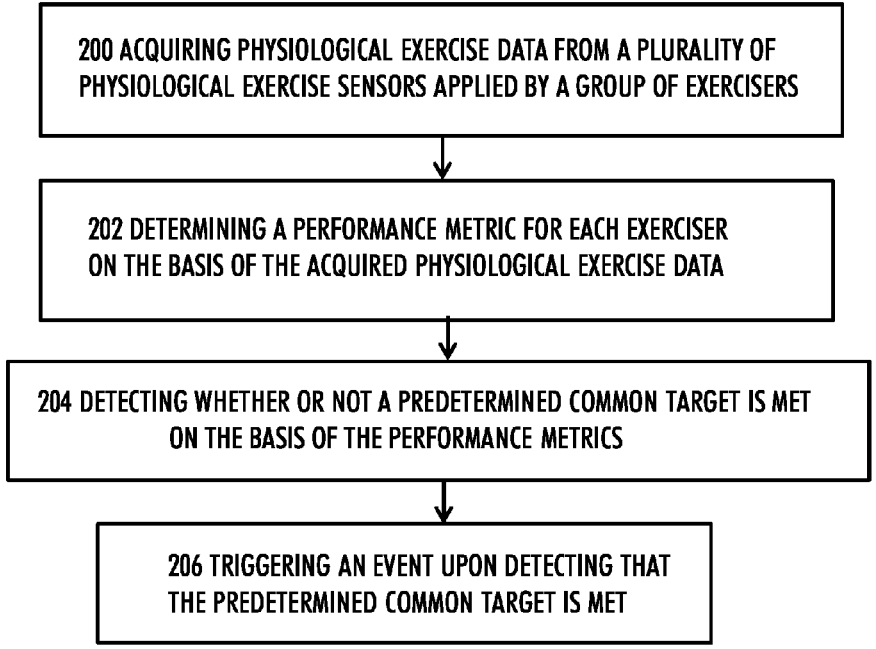
FIG. 2 shows a method according to an embodiment.

Accordingly, as shown in FIG. 2, the computing device 110 may, in step 200, acquire physiological exercise data from the plurality of physiological exercise sensors applied by a group of exercisers 102-108. The exercise data may be received wirelessly from the exerciser sensors while the exercisers 102-108 are exercising during the training session. The wireless transfer of the exercise data may apply, e.g., Bluetooth, Bluetooth Low Energy, wireless local area network (WLAN, Wi-Fi), infra-red, or cellular network connection. In another embodiment, the transfer is via a wired bus, such as a USB (Universal Serial Bus) between each exercise sensor and the computing device 110. For example, when the exercise sensor is fixed to a training device, such as to a treadmill, the wired communication may take place.

In an embodiment, the exercise sensors, which transmit the physiological exercise data, may include sensors coupled to the exerciser 102-108, such as heart activity sensors, skin temperature sensors, blood pressure sensors, or acceleration sensors. In an embodiment, the exercise sensors transmitting the physiological exercise data may include sensors integrated into the used device, such as coupled to the bicycle or treadmill which is used by the exercisers 102-108 during the group training session. These sensors may include, e.g. sensors for measuring the power output of the device, sensors measuring the distance elapsed, sensors measuring the cadence in bicycling or the stride frequency/length in walking/running. Naturally, both types of exercise sensors may be used simultaneously.

In an embodiment, the received physiological exercise data (also referred to as exercise data) may be primitive measurement data, such as ECG (Electrocardiogram) data, instantaneous heart rate values, average heart rate values averaged over a determined number of heart beats, RR intervals acquired from peak intervals of heart rate signals. In an embodiment, the received exercise data may comprise activity samples obtained from an accelerometer measurement, distance elapsed, speed and/or pace samples, power samples, cadence samples, pedal index, left-right balance, running index, training load information, energy consumption information, galvanic skin response samples, fluid balance information, blood pressure samples, skin temperature samples, to mention only a few possible options. The physiological exercise data may thus represent the physiological effort of the exerciser 102-108.

In step 202, the computing device 110 may determine a performance metric for each exerciser 102-108 on the basis of the acquired physiological exercise data. In an embodiment, the performance metric represents at least one of the following: heart activity, distance elapsed, pedalling speed, power output of a used exercise device, cadence, energy consumption rate, consumed energy, training effect, skin temperature, pedal index, left-right balance, running index, fluid balance, blood pressure.

In the case the performance metric represents heart activity, the performance metric may be heart rate or heart rate variation derived on the basis of hear activity sensor data, for example. In the case the performance metric represents pedalling speed, cadence, or power output of a used exercise device, the exercise data may be obtained from an exercise sensor coupled to the used exercise device.

In an embodiment, the performance metric represents training effect (also known as a training load or a training benefit). The training load feature may indicate how hard your training session was taking into account the training history from the past and how much time you will need to recover from the training before you train again. The training load value may be derived at any point on the basis of exercise data obtained so far. The training load may gradually decrease as resting time elapses. For example, a member of the group (let us say the person 102) may have exercised yesterday, whereas the person 104 may have rested for three days before coming to the group training session. Therefore, it is likely that the person 102 has initially a higher training load than person 104. It may also be that the exercisers 102 consequently has a higher training load during the group training session even if the exercisers 102 and 104 have exercised substantially similarly during this group training session. By applying the training load as the performance metric, the effect of tiredness and different exercising behaviour may be advantageously taken into account in a comparison between two different exercisers. For example, the same training load effect may be obtained by these two persons 102, 104 with different efforts during this group training session.

Let us then look further at FIG. 2. In step 204, the computing device 110 may detect whether or not a predetermined common target is met on the basis of the performance metrics. The common target may be anything as long as reaching the common target depends on each of the performance metrics of the plurality of exercisers. Thus, the performance of each of the exercisers 102-108 may have an effect on whether or not the common target is met. Then, in step 206, the computing device 110 may trigger an event upon detecting that the predetermined common target is met. In case the target is not met, no event is triggered.

Let us take a closer look on how the step 204 may be performed. Let us assume that the performance metric derived on the basis of the obtained exercise data is the heart rate (HR).

Figure 3A:
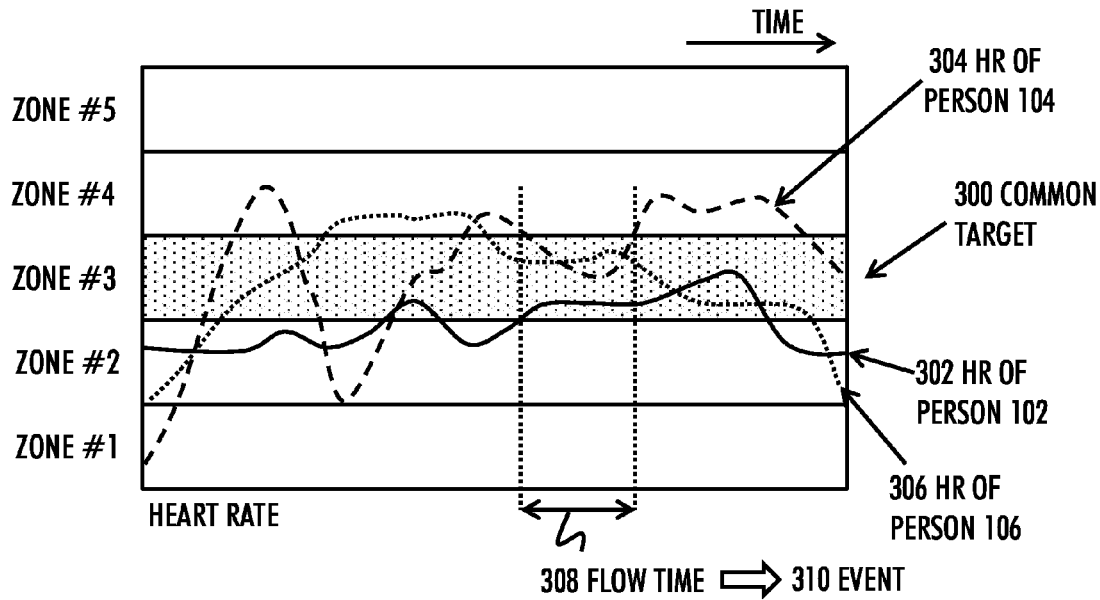
FIGS. 3A and 3B show some embodiments for determining whether or not a common target is met.

In an embodiment of FIG. 3A, solid, dotted and dashed curves 302-306 represent heart rates of the exercisers 102-106, respectively, during the group training session. The heart rate value may be presented as an absolute heart rate value or as a percentage from the maximum heart rate. The curves 302-306 may be based on the received heart activity related physiological exercise data from the exercise sensors (obtained in step 200). It may be seen that as the time elapses during the group training session, each heart rate curve 302-306 varies relatively independently of each other.

The overall heart rate range may be divided into predetermined zones #1-#5. In an embodiment, zones #1-#5 may be based on predetermined percentages of a theoretical or a measured maximum heart rate of the group. In another embodiment, the zones may be defined as beats per minute (BPM), such as 60-120 BPM (zone #1), 121-140 BPM (zone #2), 141-160 BPM (zone #3), 161-180 BPM (zone #4), and 181-220 BPM (zone #5). However, it should be noted that these ranges are non-limiting examples. Each zone may provide different benefits for the exerciser, such as to physical endurance, aerobic capacity, strength, cardiovascular fitness, fat burning, lactic acid system, anaerobic capacity, of the person 102-106.

Although HR zones are used for the sake of simplicity of the illustration, the zones #1-#5 may represent some other performance metric than the heart rate. For example, the zones may represent different ranges for any instantaneous performance metric, such as current fat burning rate, current heart rate variation, current power output, current cadence, current skin temperature, to mention only a few possibilities.

In an embodiment, the common target of the group exercise is to develop the cardiovascular fitness of the members 102-106 of the group. Let us assume that the target of the group exercise is to keep the heart rate within the zone #3. Therefore, in an embodiment, the predetermined common target 300 may be to keep the heart rate within the heart rate zone #3. Alternatively, any other zone could be selected as the common target (zone) 300 if seen appropriate from the point of view of the aim of the group training session.

Therefore, in an embodiment, it may be detected, on the basis of the determined performance metrics (HRs 302-306 of each exerciser 102-106), whether or not each of the performance metrics 302-306 fulfills the predetermined common target 300 simultaneously. In the example of FIG. 3A, this may mean determining whether or not each of the hearts rates of the exercisers 102-106 are in the common target HR zone 300. As can be seen from FIG. 3A, there is only one period of time during which each of the HRs 302-306 is in the target performance zone 300. This is shown with a reference numeral 308 and denoted as a "flow time". When it is detected that the predetermined common target 300 is met by each of the performance metrics 302-306 simultaneously, the computing device 110 may trigger the event 310. Let us later take a look at triggering the event 310. As each person's 102-106 effort affects the triggering of the event, each exerciser 102. 106 may be more motivated to perform well during the group exercise.

The flow time or (flow time period) denotes the time during which the predetermined common target 300 is met. As some examples, this may mean the period during which the predetermined common target 300 is met by each of the performance metrics 302-306 simultaneously, or a period during which the predetermined common target is met by the group (such as in case the common target is a predefined accumulated performance threshold, as will be later introduced).

In one embodiment, individual zones are determined for each exerciser 102-106. Then the common target performance zone 300 may the zone #3 for each of the exerciser 102-106 in their own individualized HR zones. The individual HR zones may be obtained from a corresponding web user account of the exercisers 102-106, or the individual HR zones may be derived prior to the exercise by using Polar OwnZone®-feature, for example. As the individual zone #3 may be different for the exerciser 102 than for the other exercisers 104 or 106, the exercisers 102-106 may be exercising within the zone #3 although having different heart rates. The computing device 110 may detect whether or not each of the exercisers 102-106 fulfills the predetermined common target 300 simultaneously according their own individualized zones. In case the answer is positive, the computing device 110 may trigger the event 310.

In an embodiment, the computing system 110 determines simultaneously each exerciser's 102-106 personal HR zones in the early stage of a training session based on heart rate variability of each exerciser 102-106.

Figure 3B:
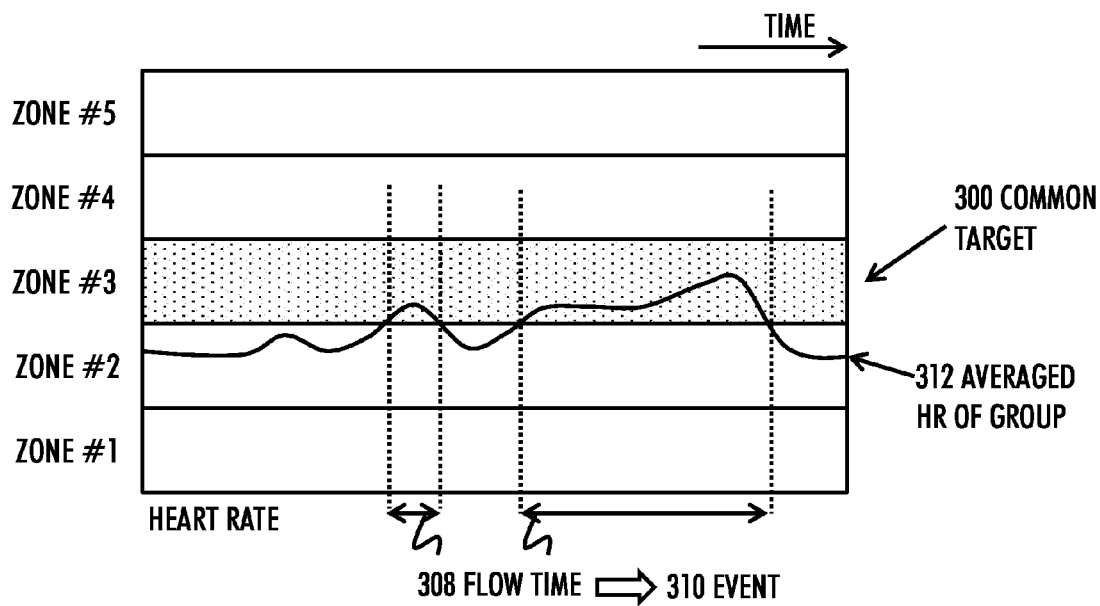

In the embodiment of FIG. 3B, the computing device 110 may average the performance metrics of the exercisers 102-106. Again, let us consider the HR as an example performance metric. The solid curve 312 in FIG. 3B represents the average of the heart rates of the exercisers 102-106. Then it may be detected whether or not the averaged performance metric 312 fulfills the predetermined common target 300. It is again assumed that the common target 300 is to keep the averaged performance metric within the zone #3. Then the computing device 110 may compare the average HR 312 to the desired heart rate zone #3. Upon detecting that the predetermined common target 300 is met by the averaged performance metric 312, the computing device 110 may trigger the event 310. As the predetermined common target 300 is met at two different time periods as can be seen from FIG. 3B, the event 310 may be triggered twice, for example. Again, as each exerciser 102-106 has a direct effect on whether or not the event 310 is triggered, it may be likely that each exerciser 102-106 wants to perform at his/her best level during the group exercise.

In an embodiment, the common target 300 may be to reach a predefined accumulated performance threshold. For example, such accumulated performance threshold may represent consumed calories or elapsed distance. In such case, the performance metrics of all the exercisers 102-106 may be summed and it may be detected whether or not the summed performance metric is higher than the accumulated performance threshold, i.e. whether or not the summed performance metric meets the predetermined common target. In case the answer is positive, the computing device 110 may trigger the event 310.

In an embodiment, the reach of the accumulated performance threshold may be determined individually. That is, it may be checked whether each and every exerciser 102-106 has consumed at least a certain amount of calories. In case the answer is positive, the computing device 110 may trigger the event 310.

In an embodiment, there may be various different common targets 300. For example, the first common target may be to consume, as a group, 1000 kilocalories (kCal) of energy, whereas the second common target may to consume 2000 kCal of energy as a group, etc. Different events 310 may be triggered upon meeting different common targets. As the first target is met, a first event may be triggered. The first event may be an instantaneous event or it may be kept active until the trigger of the second event, until the end of the group training session, or until the common target is not met anymore (in case of FIG. 3A where the flow time 308 ends), for example.

Figure 4A:
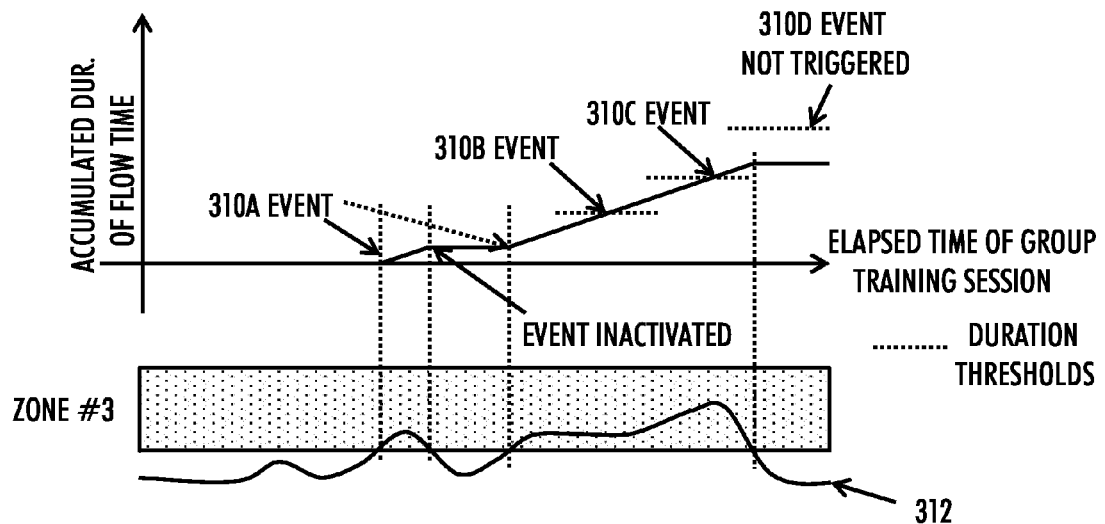
FIGS. 4A and 4B illustrate some embodiments for determining a time duration within which the common target is met.
Figure 4B:
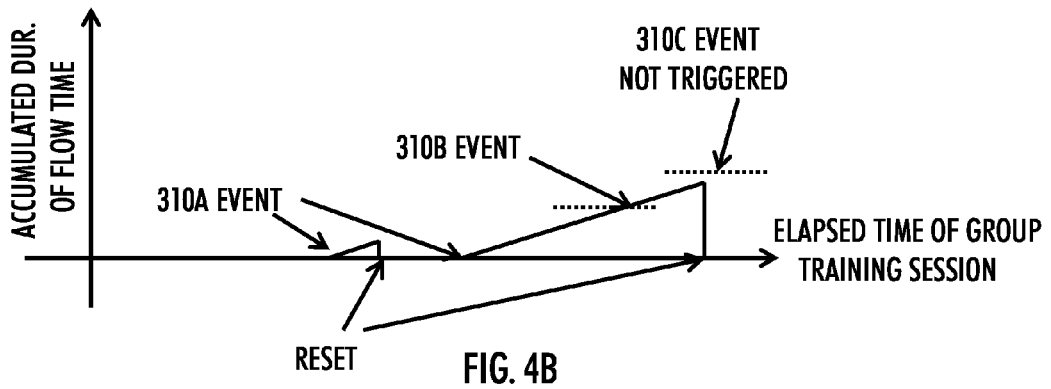

In an embodiment, as shown in FIGS. 4A and 4B, the computing device 110 may measure the accumulated time during which the predetermined common target 300 is met. That is, the computing device 110 may measure the accumulated duration of the flow time 308. The computing device 110 may trigger a first event 310A when the flow time starts, for example. Upon detecting that the accumulated duration fulfills further predetermined duration thresholds, the computing device 110 may trigger a second and a third event 310B, 310C, as shown in FIG. 4A. However, for illustration purposes in FIG. 4A the accumulated time may not reach the accumulated duration threshold corresponding to the event 310D. Therefore, this event 310D may not be triggered. In this example, the accumulated duration lasting at least until the predetermined duration threshold may be seen as one predetermined common target, which triggers an event, such as the event 310B, 310C, or 310D.

As shown in FIG. 4A, in an embodiment, the accumulated time may be accumulated throughout the group training session without reset. The cumulated duration of the flow time may be announced to exercisers 102-106 at the end of the group exercise session. This may increase the motivation of the exercisers 102-106 to put their best effort to the group training session. Moreover, the time may be saved to club records and to personal records in the user accounts of the exercisers 102-106.

However, in another embodiment, as shown in FIG. 4B, an end of each flow time period may reset the accumulated time. Thus, in this embodiment, the accumulated duration of flow time represents the accumulated continuous duration of the flow time 308. In this case, the event 310A may be triggered twice, e.g. each time the flow time starts. During the second flow time period, the event 310B may also be triggered once the corresponding accumulated duration threshold is met. However, the event 310C or 310D may not be triggered as the continuous accumulated time duration may not reach the corresponding accumulated duration thresholds. When the common target is not met, no event is being shown.

In an embodiment, the event is inactivated (e.g. not shown on the display 120) when the flow time 308 does not take place, i.e. when the common target 300 is not met. In such a case, looking at FIG. 3A, it may be seen that the event 310A is activated at the start of the first flow time. Then the event is inactivated (e.g. the display 120 shows a normal view of FIG. 1) when the flow time stops. When the flow time starts again, the event 310A may again be displayed on the screen 120.

As indicated with FIGS. 3A and 3B, for example, the predetermined common target 300 may be a common target performance zone within which the value of the performance metric is required to be. The common target performance zone may be preconfigured to the system or it may be given in another manner. In an embodiment, the common target performance zone is defined on the basis of the performance metric of one of the following: a plurality of members of the group, an individual member 102, 104 or 106 of the group, an instructor 100 of the group.

Figure 5:
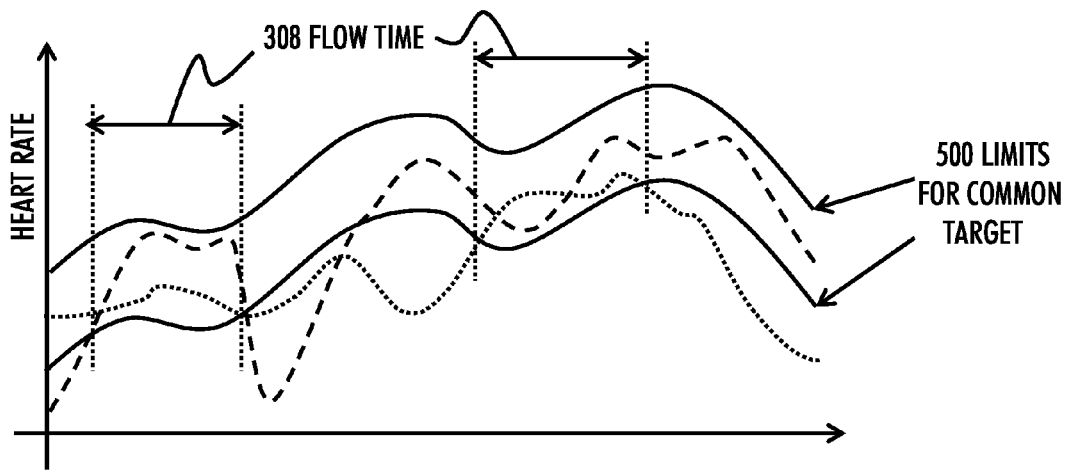
FIG. 5 depicts yet one embodiment for determining whether or not the common target is met.

For example, in FIG. 5, the limits 500 for the common target zone are defined by the heart rate of the instructor 100. The instructor's 100 HR with predetermined margins may then serve as the common target zone within which the averaged HR or the individual HRs (marked with dotted and dashed curves in FIG. 5) are supposed to be in order to start the flow time 308 and trigger the event 310. In this embodiment, the target zone may vary and make the group training more interesting and dynamic experience for the exercisers 102-106. As may be the case with non-varying target zone of FIGS. 3A and 3B, also in the example of FIG. 5, the varying target HR area/zone may be shown to the exercisers 102-106 via the display 120 so that the exercisers 102-106 may keep track of what the heart rate is desired to be at a given time instant. Alternatively, the limits 500 may be set by the HR of an individual member of the group, e.g. the HR of the exerciser 102, wherein the HR of the user 102 is accompanied with predetermined margins, such as +/−10 BPM, as a non-limiting example.

Figure 6:
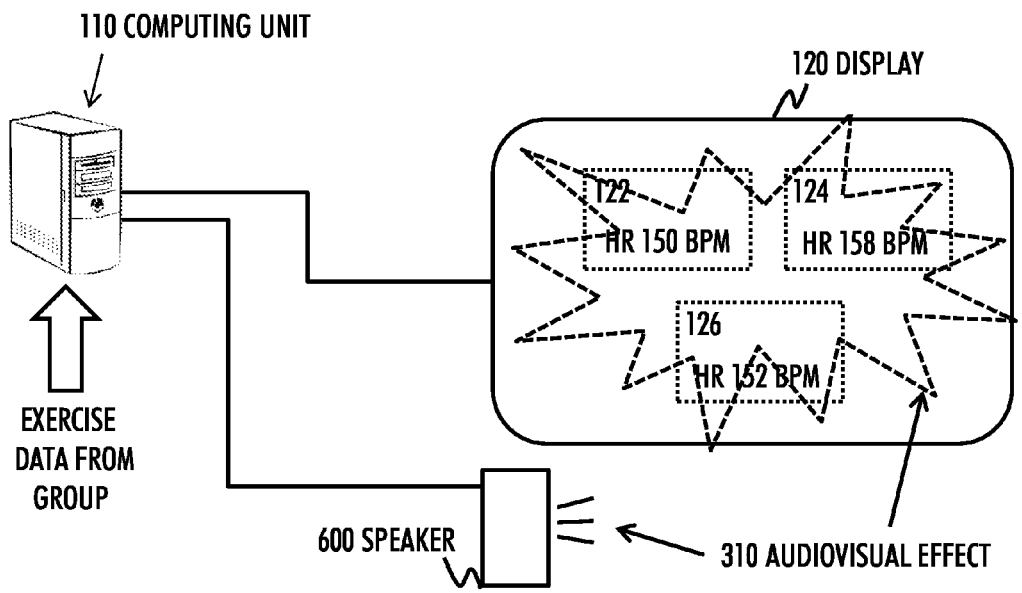
FIG. 6 illustrates how an event is triggered, according to an embodiment.

Let us then consider the event 310 with reference to FIG. 6. In an embodiment, the event may be, e.g., a visual effect on the display 120, a sound from a speaker 600, an audio-visual effect detectable by the exercisers 102-108. In an embodiment, the event 310 changes the view on the display 120. As the event 310 is triggered and active only when the common target is met, the event 310 provides an effective and easy to understand message which may turn the group exercise sessions more interesting. Such group activity based event 310 provides an ability to achieve as a group which may be motivating.

In an embodiment, as shown in FIG. 6, the computing device 110 may, on the basis of the exercise data from the group, trigger the activation of the event 310 via an output unit, such as the display 120 or the speaker 600. For example, when all exercisers 102-106 of the group are at the same heart rate zone (common target 300), the screen 120 may show a visual effect, such as an image displayed on the display 120 or the screen 120 may start to flash/glow. The exercisers 102-106 may be able to see this from the display 120 so that the exercisers 102-106 may know that the flow time has started accumulating. Then the exercisers 102-106 may try more hard to stay in the target zone or to follow the target zone determined by the instructor 100, for example. When at least one exerciser drops from desired common target zone, the event 310 may be inactivated and, e.g., the display 120 may stop glowing. When the common target is again met by each of the exercisers 102, 106, the event may be triggered again. At the end of the group training session, the reached accumulated time duration of the flow time may be shown to participants and possibly added to the cumulative flow time (as shown in FIG. 4A) or reset (as shown in FIG. 4B).

Figure 7:
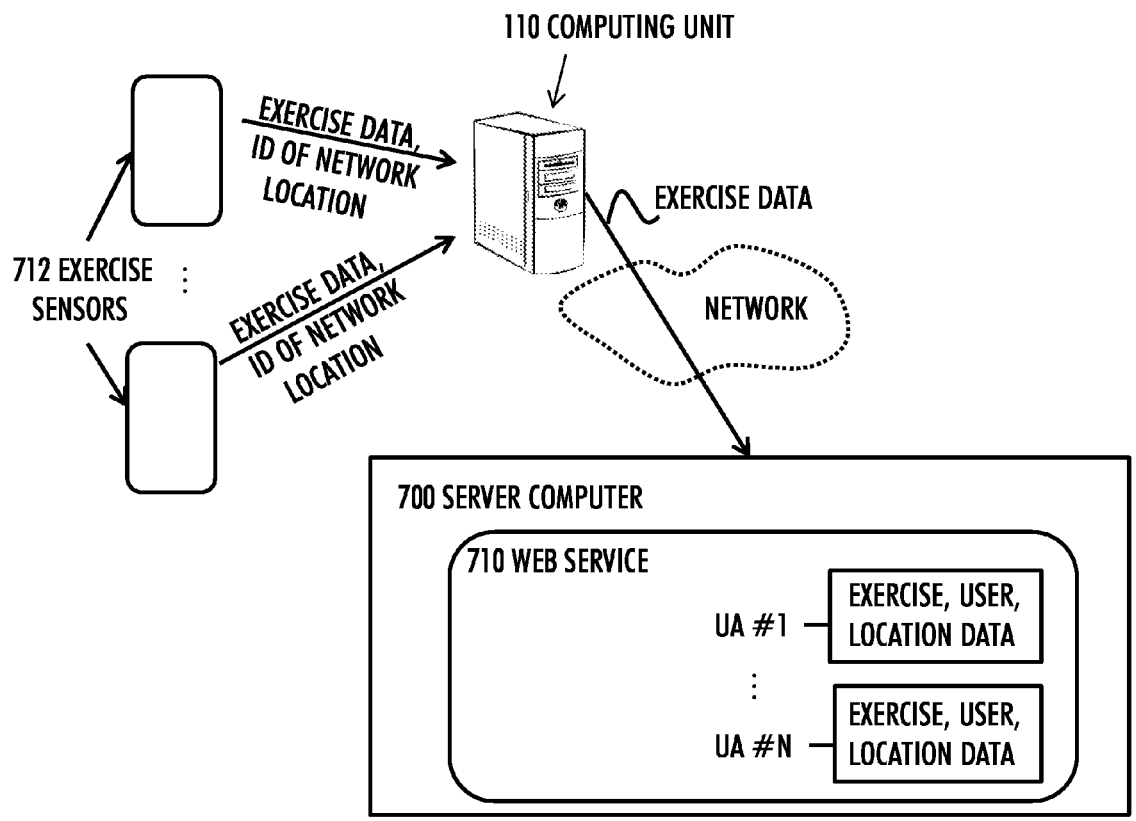
FIG. 7 shows storing of data to a user account, according to an embodiment.

In an embodiment shown in FIG. 7, the computing device 110 may obtain, from each of the exercise sensors 712 applied by the exercisers 102-106, information indicating a user account corresponding to the exerciser 102-106 applying the physiological exercise sensor 712. That is, in addition to the obtained exercise data, the computing device 110 may receive also an indication of user accounts of the exercisers 102-106. The user account may be located in a predetermined server 700 in the network. Each user account (UA) may comprise exercise data associated with a specific user. As such, there may be different user accounts for different users #1, #2, . . . , and #N. The server 700 may further host and provide a web service 710 accessible by end users via a user interface on a client's device, such as a personal computer, a tablet, a smart phone, etc. An example of such a web service 710 may be a Polar Personal Trainer (PTT), Polar Flow or iFIT service.

The information identifying the user account may be given with at least one of the following: an internet protocol (IP) address of the server 700, static or dynamic uniform resource identifier/locator (URI/URL)) of the server 700, a medium access control (MAC) address of the exercise sensor 712. By identifying the location of the server 700, the computing device 110 may be able to direct the exercise data to a correct server 700 on the internet. By knowing the MAC address or another identifier of the exercise sensor 712, the server 700 may be able to access the correct user account which is associated with the given identifier of the exercise sensor 712. In this manner, the computing device 110 may be able to cause storage of the acquired physiological exercise data in the indicated user account. In one embodiment, the computing device 110 itself has preconfigured knowledge of the associations between the user accounts on the web service 710 and the identifiers of the exercise sensors 712. In this case, the computing device 110 may indicate the user account to the server 700 directly.

The associations between the user accounts on the web service 710 and the identifiers of the exercise sensors 712 may be obtained due to the end users (e.g. exercisers 102-106) registering their exercise products (e.g. exercise sensors 712) to the web service 710. For example, in an embodiment, the web service 710 may require that the users connect to the web service 710 by applying a user name and a password, or other identification means, via their end user devices. Once allowed to access, the user may register products to the web service 710. In this way, the web service 710 may know which products (e.g. sensors 712) belong to which users. The user may also transfer, e.g., training data from their exercises devices 712 to the user accounts. The user may also change the settings of his/her exercise device(s) 712 in the web service 710 and download the exercise device's settings from the web service 710 via the network to the exercise device 712, for example.

Alternatively, the registration of user accounts and used exercise sensors 712 may be performed in the computing device 110. For example, prior to starting the group exercise, the exercisers 102-108 may be provided with exercise sensors 712 by the instructor 100. A user account of the exerciser 102 may be associated with the exercise sensor(s) 712 that was/were given to the exerciser 102 for use during the group training session. The associations may be stored in the computing device 110. As exercise data and ID of the exercise sensor 712 is acquired during the workout from the exerciser 102, the computing device 110 may check the recently built association table and know that data from this sensor ID needs to be stored to that user account in the specified server 700 of the internet. The association may be valid only for the duration of the group training session after which the exercisers 102-106 may return the exercise sensors 712 back to the instructor 100, for example.

The user accounts may also store, with respect to the corresponding user, user attributes such as name, gender, age, weight, height, fitness level, training history comprising measurement data and accumulated performance data, training schedule, maximum oxygen intake (VO2Max), maximum heart rate (HRMax), performance zones (heart rate zones, speed zones), aerobic and anaerobic thresholds, etc. For example, in the embodiment in which it is detected whether the heart rate of a given user stays within the heart rate zone #3 of the individual heart rate zones of that user, these individual heart rate zones may be downloaded from the user account of the server 700 once the exercise has identified his/her user account to the computing device 110.

Moreover, the associations between the users 102-106 and the exercise sensors 712 may be checked when the performance metrics are displayed on the display 120, as shown in FIGS. 1 and 6.

In an embodiment, personal cumulated flow times may be stored to the corresponding user accounts of the group members. The personal flow time of the exerciser 102 may be increased as the exerciser 102 takes part in another group exercise, possible with another group. The personal flow time-parameter increases only when the exerciser 102 is a member of a group which, as a group, meets the common target so that flow time 308 starts accumulating. For example, the exerciser 102 participates in two group trainings. The first group is able to meet the flow time criterion for 10 minutes (in parts or as one continuous flow time period) whereas the second group meets the flow time criterion for 15 minutes. Then the personal flow time parameter gets a value of 25 minutes after these two group trainings, regardless of how long the exerciser 102 himself/herself kept his/her heart rate within the desired common target zone. In this way, the exerciser 102 may be motivated to take part in many group exercises and perform well in the group exercises, and also to motivate others to perform well, so as to increase the value of the personal flow time-parameter stored in the corresponding user account on the server 700.

In addition to providing group based rewards in the form of display of events 310 and personal flow time-parameters, individual achievements may also be rewarded. In an embodiment, the computing device 110 is caused to determine on the basis of the physiological exercise data which exerciser 102-106 has the greatest variation of the performance metric during the training session. For example, looking at FIG. 3A, the exerciser 104 corresponding to the HR curve 304 has the largest variation of the heart rate as the performance metric.

In an embodiment, the computing device 110 is caused to determine on the basis of the physiological exercise data which exerciser has the fastest recovery with respect to the performance metric. Although not shown in Figures, this may be determined by measuring the performance metric until a predetermined time after the end of the group training session. For example, the exerciser 102-106 whose heart rate decreases the fastest below the aerobic threshold (detectable from exerciser's user accounts, for example), may be selected as the exerciser with the fastest recovery.

In an embodiment, the computing device 110 is caused to determine on the basis of the physiological exercise data which exerciser meets the predetermined common target the longest. This may be determined by comparing the performance metrics, such as the HR curves 302-306 against the target zone. For example, in FIG. 5, the exerciser corresponding to the dashed HR curve may be selected as the "zone master", as he/she has stayed within the target zone longer than the exerciser associated with the dotted HR curve.

In an embodiment, the computing device 110 is caused to determine on the basis of the physiological exercise data which two exercisers have the most similar behaviour of the performance metrics. This may be determined by comparing different performance metrics, such as by comparing the heart rate curves 302-306. The computing device 110 may calculate cross-correlations between different heart rate curves 302-306 to determine which two curves 302-306 are the most similar, for example.

Thereafter, the computing device 110 may output an identifier of the determined exerciser or exercisers via the display 120. The identifier may be a name(s) of the exerciser(s) or the location where he/she/they are exercising in the group. This may motivate the exercisers 102-106 to perform well during the group exercise also.

Figure 8:
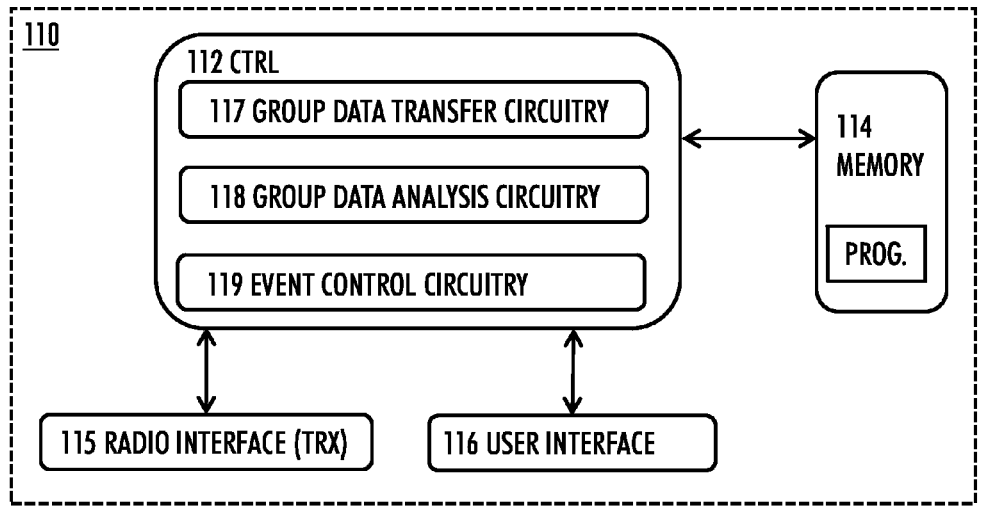
FIG. 8 illustrates an apparatus, according to an embodiment.

In an embodiment, the computing device 110 is a local computing device on the premises of the group exercise. An example device may be a tablet computer, a smart phone, or a PC/MAC. In an embodiment, such local computing device 110 is not connected to Internet. FIG. 8 shows an example of the computing device 110, comprising a control circuitry (CTRL) 112, such as at least one processor, and at least one memory 114 including a computer program code (PROG), wherein the at least one memory 114 and the computer program code (PROG), are configured, with the at least one processor 112, to cause the apparatus 110 to carry out any one of the described processes. The memory 114 may be implemented using any suitable data storage technology, such as semiconductor based memory devices, flash memory, magnetic memory devices and systems, optical memory devices and systems, fixed memory and removable memory.

The apparatus may further comprise communication interface (TRX) 115 comprising hardware and/or software for realizing communication connectivity according to one or more communication protocols (e.g. WLAN, Bluetooth, Bluetooth low energy, cellular network). The TRX may provide the apparatus with communication capabilities for receiving the exercise data, for example. Optionally, the TX 115 may provide the apparatus 110 with capabilities to access the Internet and the server 700, for example.

The apparatus 110 may also comprise a user interface 116 comprising, for example, at least one keypad, a microphone, a touch display, a display, a speaker, etc. The user interface 116 may be used to control the apparatus 110 by the user. For example, the associations between the users 102-106 and the exercise sensors 712 may be made via the user interface 116.

The control circuitry 112 may comprise a group data transfer circuitry 117 for transferring data from the exercise sensors 712 and further to transfer the data to the user accounts in the server 700, according to any of the embodiments. A group data analysis circuitry 118 may be for analysing the exercise data from each of the plurality of exercisers 102-106, such as for deriving the performance metrics for each of the exercisers 102. 106. An event control circuitry 119 may be for controlling the execution/activation of the predetermined event when the common target is met.

Figure 9:
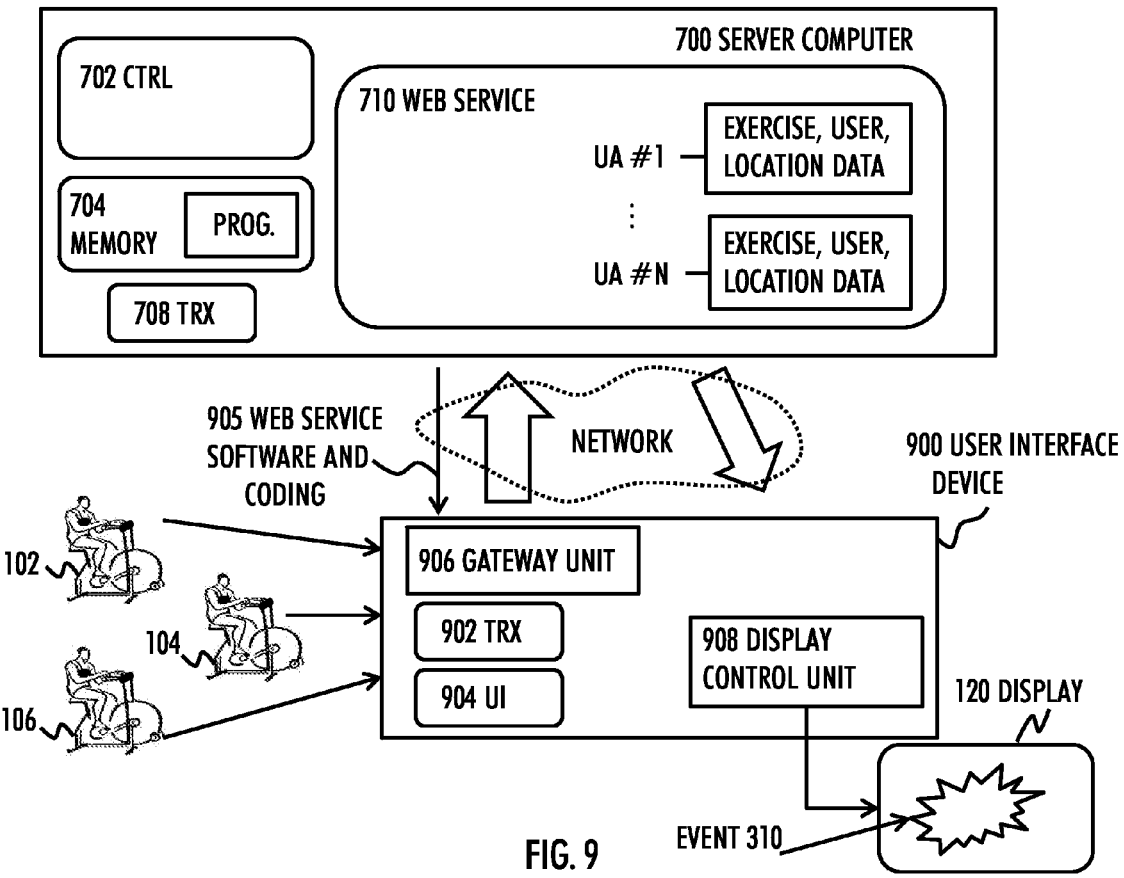
FIG. 9 depicts a scenario in which a server computer is applied, according to an embodiment.

However, in another embodiment, as shown in FIG. 9, the computing device 110 is the server computer 700 accessible via the network. The server computer 700 may comprise a control circuitry (CTRL) 702, such as at least one processor, and at least one memory 704 including a computer program code (FROG), wherein the at least one memory 704 and the computer program code (FROG), are configured, with the at least one processor 702, to cause the apparatus 700 to carry out any one of the described processes. These may include acquiring the physiological exercise data from the plurality of physiological exercise sensors applied by the group of exercisers, determining the performance metric for each exerciser on the basis of the acquired physiological exercise data, detecting whether or not the predetermined common target is met on the basis of the performance metrics, and activating the event upon detecting that the predetermined common target is met. The server 700 may also comprise a communication interface 708 for connection to the network.

There may also be a user interface device 900 on the premises of the group exercise. In addition to needed processor(s) and memory, the user interface unit/device 900 may comprise a communication interface (TRX) 902 for reception and transmission of the exercise data. Further, the user interface device 900 may comprise a user interface 904 for controlling the device 900 by a user.

In the system of FIG. 9, a gateway unit 906 of the user interface device 900 may receive and transmit the exercise data to the server 700. In addition, identification information of the exercise sensors 712, exercisers and/or user accounts may be transmitted to the server 700. The user interface device 900 may be a tablet computer, a smart phone, or a PC, for example.

The server computer 700 may then, upon detecting that the predetermined common target is met by each of the exercisers simultaneously, transmit a command to a display control unit 908 via the network. The display control unit 908 may then, as a response to the command, cause the event 310 to be activated on the display 120 viewable by the exercisers 102-106. The event 310 may be preconfigured to the memory of the user interface device 900 or the command from the server 700 may indicate what type of event is to be activated on the display 20 (e.g. how to change the view of the display 120). The embodiment of the FIG. 9 offers simplicity from the point of view of the local user interface device 900, as the data processing is mostly performed on the server computer 700.

The server computer 700 may be further caused to provide/upload web service software and required coding 905 for a web service accessible with a web browser of the user interface device 900 (client device). The memory 704 of the server 700 may comprise a computer program code (FROG), which may comprise a server code executable by the server 700 and client code (such as Hyper Text Markup Language (HTML), or a comparable mark-up language), out of which the latter may be uploaded to the client (i.e. to the user interface device 900). These codes may be executed by the server 700 and/or by the client's device 900 and cause the user device 900 to display the web service on the user's device 900.

In an embodiment, the codes may be executed as server-side scripting, which may involve embedding scripts in an HTML source code. Such server side scripting may result in a users (client's) request to the server being handled by a script running at the server-side before the server responds to the client's request. The scripts can be written in any known server-side scripting languages available, such as Java, Python or C-language. Those scripts may be executed by the operating system of the server 700, and the results may be served to the client. The server 700 may thus comprise computer software that may respond to the client's web browsers request.

As an alternative to the server side scripting, client-side scripting may be applied in which embedded scripts, such as JavaScript or HTML, are run at the client-side in the web browser of the user's device 900. Such client-side scripts may be embedded within a HTML or extensible HTML (XHTML) document but they may also be contained in a separate file, to which the document (or documents) that use it make reference. Upon request, the necessary files are sent to the user's computer 900 by the server 700 on which they reside, for example according to a Hypertext Transfer Protocol (HTTP) or a File Transfer Protocol (FTP) communication protocols. The users web browser may then execute the script, display the document, including any visible output (such as user interface at the client's device 900) according to the executed code. The client-side scripts may also contain instructions for the web browser to follow certain user actions, (e.g., clicking a button). Yet, in one embodiment, the server-side scripting may be combined with the client-side scripting.

Owing to the provided software and coding 805, the instructor 100 may start the software (web service) on the user interface device 900 prior to the users 102-106 start exercising in the group training session. The software may then cause the device 900 to start transmitting any received data from the exercisers sensors 712 of the exercisers 102-106 via the network to a preconfigured destination where the server 700 resides and to detect any commands from the server 700.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rear-ranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A system, comprising:
a plurality of physiological exercise sensors associated with at least one of an exercise device, a first exerciser, or a second exerciser;
a display;
at least one processor; and
at least one memory including a computer prog-ram code, wherein the at least one memory and the computer program code are configured, with the at least one processor, to cause the system to perform operations comprising:
acquiring physiological exercise data in an electronic format using the plurality of physiological exercise sensors applied by the first exerciser and the second exerciser, the plurality of physiological exercise sensors comprising at least one of a heart activity sensor, a cadence sensor, or a power sensor;
determining a first performance metric for the first exerciser and a second performance metric for the second exerciser on the basis of the acquired physiological exercise data;
detecting whether or not a predetermined common target is collectively fulfilled by the first and second exercisers on the basis of the first and second performance metrics;
triggering an event in response to detecting that the first and second exercisers collectively fulfill the predetermined common target such that the first and second exercisers have a direct effect on whether or not the event is triggered;
detecting whether or not the first performance metric and the second performance metric individually fulfill the predetermined common target simultaneously;
triggering the event in response to detecting that the first performance metric and the second performance metric individually fulfill the predetermined common target simultaneously such that the first and second exercisers have a direct effect on whether or not the event is triggered; and
displaying the event on the display to at least one of the first exerciser or the second exerciser.

2. The system of claim 1, wherein the at least one memory and the computer program code are configured, with the at least one processor, to cause the system further to perform operations comprising:
determining an averaged performance metric by averaging the first performance metric of the first exerciser and the second performance metric of the second exerciser;
detecting whether or not the averaged performance metric fulfills the predetermined common target; and
triggering the event upon detecting that the predetermined common target is met by the averaged performance metric.

3. The system of claim 1, wherein there is a plurality of different common targets, and wherein the at least one memory and the computer program code are configured, with the at least one processor, to cause the system further to perform operations comprising:
triggering different events upon meeting the plurality of different common targets.

4. The system of claim 1, wherein the at least one memory and the computer program code are configured, with the at least one processor, to cause the system further to perform operations comprising:
measuring an accumulated time during which the predetermined common target is met; and
triggering, upon detecting that the accumulated time fulfills a predetermined duration threshold, a second event.

5. The system of claim 1, wherein the first performance metric and the second performance metric individually fulfill the predetermined common target simultaneously when a first value of the first performance metric and a second value of the second performance metric are simultaneously within a common target performance zone.

6. The system of claim 5, wherein the at least one memory and the computer program code are configured, with the at least one processor, to cause the system further to perform operations comprising defining the common target performance zone based on a third performance metric of one of the following: a plurality of members of a group, an individual member of the group, or an instructor of the group.

7. The system of claim 1, wherein at least one of the first performance metric or the second performance metric represent at least one of the following: heart activity, distance elapsed, pedalling speed, power output of a used exercise device, cadence, energy consumption rate, consumed energy, training effect, skin temperature, pedal index, left-right balance, running index, fluid balance, blood pressure.

8. The system of claim 1, wherein the at least one processor is operatively coupled to the display, and wherein the at least one memory and the computer program code are configured, with the at least one processor, to cause the system further to perform operations comprising:
changing a view of the display when the event is triggered.

9. The system of claim 1, wherein the at least one memory and the computer program code are configured, with the at least one processor, to cause the system further to perform operations comprising:
obtaining, from each of the plurality physiological exercise sensors, information indicating a user account corresponding to one of the first exerciser or the second exerciser applying one of the plurality of physiological exercise sensors, wherein the user account is located in a predetermined server in a network; and causing a storage of the acquired physiological exercise data in the indicated user account.

10. The system of claim 1, wherein the computing device is a server computer, and wherein the at least one memory and the computer program code are configured, with the at least one processor, to cause the system further to perform operations comprising:

providing a web service to a client device;

receiving the physiological exercise data via a network from the web service of the client device; and transmit a command to a display controller of the client device via the network, wherein the display controller, as a response to the command, causes the event to be activated on the display viewable by the exercisers.

11. The system of claim 1, wherein the at least one memory and the computer program code are configured, with the at least one processor, to cause the system further to perform operations comprising:

determining at least one of the following on the basis of the physiological exercise data: which exerciser has the fastest recovery, which exerciser meets the predetermined common target longest; and outputting an identifier of the determined exerciser or exercisers via the display.

12. A method, comprising:

acquiring physiological exercise data in an electronic format using a plurality of physiological exercise sensors applied by a first exerciser and a second exerciser, the plurality of physiological exercise sensors being associated with at least one of an exercise device, a first exerciser, or a second exerciser, the plurality of physiological exercise sensors comprising at least one of a heart activity sensor, a cadence sensor, or a power sensor;

determining a first performance metric for the first exerciser and a second performance metric for the second exerciser on the basis of the acquired physiological exercise data;

detecting whether or not a predetermined common target is collectively fulfilled by the first and second exercisers on the basis of the first and second performance metrics;

triggering an event in response to detecting that the first and second exercisers collectively fulfill the predetermined common target such that the first and second exercisers have a direct effect on whether or not the event is triggered;

detecting whether or not the first performance metric and the second performance metric individually fulfill the predetermined common target simultaneously;

triggering the event in response to detecting that the first performance metric and the second performance metric individually fulfill the predetermined common target simultaneously such that the first and second exercisers have a direct effect on whether or not the event is triggered; and displaying the event on a display to at least one of the first exerciser or the second exerciser.

13. A computer program product embodied on a non-transitory distribution medium readable by a computer and comprising program instructions that, when executed by a processing device, cause the processing device to perform operations comprising:

acquiring physiological exercise data in an electronic format using a plurality of physiological exercise sensors applied by a first exerciser and a second exerciser, the plurality of physiological exercise sensors being associated with at least one of an exercise device, a first exerciser, or a second exerciser, the plurality of physiological exercise sensors comprising at least one of a heart activity sensor, a cadence sensor, or a power sensor;

determining a first performance metric for the first exerciser and a second performance metric for the second exerciser on the basis of the acquired physiological exercise data;

detecting whether or not a predetermined common target is collectively fulfilled by the first and second exercisers on the basis of the first and second performance metrics;

triggering an event in response to detecting that the first and second exercisers collectively fulfill the predetermined common target such that the first and second exercisers have a direct effect on whether or not the event is triggered;

detecting whether or not the first performance metric and the second performance metric individually fulfill the predetermined common target simultaneously;

triggering the event in response to detecting that the e first performance metric and the second performance metric individually fulfill the predetermined common target simultaneously such that the first and second exercisers have a direct effect on whether or not the event is triggered; and displaying the event on a display to at least one of the first exerciser or the second exerciser.

14. An apparatus, comprising:

a plurality of physiological exercise sensors associated with at least one of an exercise device, a first exerciser, or a second exerciser;

a display;

at least one processor and at least one memory including a computer program code, wherein the at least one memory and the computer program code are configured, with the at least one processor, to cause the apparatus to perform operations comprising:

acquiring physiological exercise data in an electronic format using the plurality of physiological exercise sensors applied by the first exerciser and the second exerciser, the plurality of physiological exercise sensors comprising at least one of a heart activity sensor, a cadence sensor, or a power sensor;

determining a first performance metric for the first exerciser and a second performance metric for the second exerciser on the basis of the acquired physiological exercise data;

detecting whether or not a predetermined common target is collectively and individually fulfilled by the first and second exercisers on the basis of the first and second performance metrics; and triggering an event in response to detecting that the first and second exercisers collectively and individually fulfill the predetermined common target such that the first and second exercisers have a direct effect on whether or not the event is triggered, wherein the performance metric represents at least one of pedalling speed, pedalling cadence, energy consumption rate, pedal index; and displaying the event on the display to at least one of the first exerciser or the second exerciser.

* * * * *